United States Patent [19]

Rosenberger

[11] 4,390,735
[45] Jun. 28, 1983

[54] PROCESS FOR THE PREPARATION OF P-ALLYLPHENOLS

[75] Inventor: Siegfried Rosenberger, Riehen, Switzerland

[73] Assignee: Ciba-Geigy Corporation, Ardsley, N.Y.

[21] Appl. No.: 310,709

[22] Filed: Oct. 13, 1981

[30] Foreign Application Priority Data

Oct. 22, 1980 [CH] Switzerland .................. 7873/80

[51] Int. Cl.³ .................. C07C 37/18; C07C 37/11
[52] U.S. Cl. .................. 568/790; 568/743; 568/744
[58] Field of Search ........... 568/780, 790, 743, 744

[56] References Cited

U.S. PATENT DOCUMENTS

| 2,968,679 | 1/1961 | Aeloy | 568/780 |
| 3,198,842 | 8/1965 | Berrigan | 568/780 |
| 3,526,668 | 9/1970 | Starnes et al. | |

OTHER PUBLICATIONS

C. Starks, Chemtech, Feb. 1980, 110.

Primary Examiner—Werren B. Lone

Attorney, Agent, or Firm—Luther A. R. Hall

[57] ABSTRACT

A process for the preparation of a p-allylphenol of the formula I, which comprises reacting a phenol of the formula II with an allyl halide of the formula III

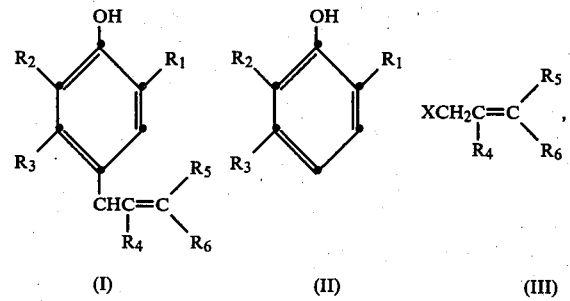

in which the symbols $R_1$ to $R_6$ and X are as defined in the description, in the presence of a base and a phase transfer catalyst.

p-Allylphenols are valuable intermediates and lubricant additives.

11 Claims, No Drawings

PROCESS FOR THE PREPARATION OF P-ALLYLPHENOLS

The present invention relates to a process for the preparation of p-allylphenols from phenols, having at least one substituent in the ortho-position, and allyl halides, and to the use of the p-allylphenols as lubricant additives.

U.S. Pat. No. 3,526,668 describes a process for the preparation of p-allylphenols, wherein an alkali metal salt of a 2,6-disubstituted phenol is reacted with a primary allyl halide in a preferably polar, aprotic solvent. However, this process is expensive and the yields of p-allylphenol are unsatisfactory. Since p-allylphenols are valuable antioxidants and intermediates, the process needs to be improved.

It has now been found that substantially higher yields of p-allylphenol can be obtained when the phenol and allyl halide are reacted in the presence of a phase transfer catalyst. At the same time, the formation of the phenolate in a separate process step is eliminated, the reaction times are shorter and the isolation of the p-allylphenol is simplified.

The present invention relates to a process for the preparation of p-allylphenols, which comprises reacting phenols, which are substituted in the ortho-position, with allyl halides in the presence of a base and a phase transfer catalyst.

Preferably, p-allylphenols of the formula I are prepared by the process according to the invention from phenols of the formula II and allyl halides of the formula III

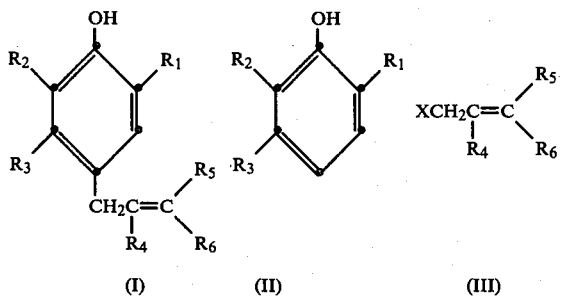

in which $R_1$ and $R_2$ independently of one another are $C_1-C_{12}$ alkyl, phenyl, $C_7-C_9$ aralkyl or $C_5-C_7$ cycloalkyl, and $R_2$ additionally can be hydrogen or chlorine, $R_3$ is hydrogen or methyl, $R_4$, $R_5$ and $R_6$ independently of one another are hydrogen, phenyl or $C_1-C_{20}$ alkyl, with the proviso that, as alkyl radicals, $R_4$, $R_5$ and $R_6$ in total contain 1 to 20 C atoms, and X is halogen.

$C_1-C_{12}$ Alkyl radicals $R_1$ and $R_2$ are, for example, methyl, ethyl, isopropyl, sec.-butyl, tert.-butyl, tert.-amyl, n-hexyl, 1,1,3,3-tetramethylbutyl or 1,1,3,3,5-hexamethylhexyl. Preferred alkyl groups have 1 to 8 C atoms and, moreover, $R_1$ in preferred compounds is tert.-butyl, tert.-amyl or 1,1,3,3-tetramethylbutyl.

$C_7-C_9$ Aralkyl radicals $R_1$ and $R_2$ can be benzyl, α-phenylethyl or α,α-dimethylbenzyl.

$C_5-C_7$ Cycloalkyl radicals $R_1$ and $R_2$ are cyclopentyl, cyclohexyl or cycloheptyl.

The preferred meaning of $R_3$ is hydrogen.

$C_1-C_{20}$ Alkyl radicals $R_4$, $R_5$ and $R_6$ are, for example, methyl, ethyl, isopropyl, sec.-butyl, n-hexyl, 2,2,4,4-tetramethylpentyl, straight-chain or branched dodecyl, tetradecyl, octadecyl or eicosyl. Preferred alkyl groups have 1 to 6 C atoms and, with particular preference, these are ethyl groups and especially methyl groups. The halogen X is, for example, chlorine, bromine or iodine, in particular chlorine.

The sum of the C atoms contained in the substituents $R_4$, $R_5$ and $R_6$ should be 1 to 20 in total, preferably 1 to 6 and especially 1 to 2. The most important compounds of the formula I are, amongst others, those in which one of the radicals $R_4$, $R_5$ and $R_6$ is hydrogen and the other two are methyl, and also those in which two of the radicals $R_4$, $R_5$ and $R_6$ are hydrogen and the third is methyl, and finally those in which $R_4$, $R_5$ and $R_6$ are hydrogen.

Particularly preferably, p-allylphenols of the formula I are prepared by the process according to the invention from phenols of the formula II and allyl halides of the formula III, in which $R_1$ and $R_2$ independently of one another are $C_1-C_8$ alkyl, and $R_2$ additionally can be hydrogen, $R_3$ is hydrogen or methyl and $R_4$, $R_5$ and $R_6$ independently of one another are hydrogen or $C_1-C_6$ alkyl, with the proviso that, as alkyl radicals, $R_4$, $R_5$ and $R_6$ in total contain 1 to 6 C atoms.

Especially, p-allylphenols of the formula I are prepared by the process according to the invention from phenols of the formula II and allyl halides of the formula III, in which $R_1$ and $R_2$ independently of one another are tert.-butyl, tert.-amyl or 1,1,3,3-tetramethylbutyl and $R_3$, $R_4$, $R_5$ and $R_6$ are hydrogen.

4-Allyl-2,6-di-tert.-butylphenol is a typical and particularly preferred compound of the formula I, which is prepared by the process according to the invention.

In the process according to the invention, the reactants phenol and allyl halide can be employed in stoichiometric quantities. In some cases, however, it can be advantageous to employ an excess of one of the two reactants. The excess can be up to one mol equivalent. Preferably, 0.8 to 1.4 mols of allyl halide are employed per mol of phenol.

The process according to the invention is carried out in the presence of a base which can be employed, in particular, in a quantity of at least one mol equivalent relative to the reactant phenol. Examples of suitable bases are alkali metal hydroxides, such as sodium hydroxide, potassium hydroxide or lithium hydroxide, or alkali metal carbonates, such as sodium carbonate, potassium carbonate or lithium carbonate, or alkali alcoholates having 1 to 6 C atoms, such as sodium, potassium or lithium methylate, ethylate, propylate or tert.-butylate. Preferably, alkali metal hydroxides, in particular sodium hydroxide, are used as the base.

The process according to the invention is carried out in the presence of a phase transfer catalyst which can be employed, in particular, in a quantity of 0.001 to 50 mol %, preferably 0.01 to 0.3 mol %, relative to the reactant phenol. For the process according to the invention, the conventional phase transfer catalysts described in the literature, for example those listed in CHEMTECH, February 1980, page 111, Table 1, are suitable, namely, for example, quaternary salts, cyclic polyethers, open-chain polyethers, N-alkylphosphoramides or methylene-bridged phosphorus oxides or sulfur oxides. The preferred phase transfer catalysts used in the process according to the invention are quaternary salts, such as quaternary ammonium salts or phosphonium salts, in particular the halides.

Examples of quaternary ammonium salts or phosphonium salts are: tetrabutylammonium bisulfate, tetrabutyl-, tetrahexyl-, trioctylmethyl-, trioctylethyl-, hexyltriethyl-, octyltriethyl-, decyltriethyl-, dodecyltriethyl-, hexadecyltrimethyl-, hexadecyltriethyl-, benzyltriethyl-, benzyltributyl-, tricaprylmethyl- and triphenylmethyl- ammonium or -phosphonium chloride, bromide and iodide.

The process according to the invention can be carried out without a solvent. However, the additional use of a solvent is preferred. Examples of suitable solvents are aliphatic and aromatic hydrocarbons, such as pentane, hexane, heptane, octane, nonane, decane, petroleum ether, benzene, toluene and xylene, ethers, such as diethyl ether, dibutyl ether, tetrahydrofuran and dioxane, and also chlorinated hydrocarbons, such as methylene chloride, chloroform, dichloroethane and carbon tetrachloride. Preferably, aromatic hydrocarbons, in particular toluene, are used as the solvent.

In the process according to the invention, the two-phase system preferably consists of a solid phase and a liquid phase. If water is also used, it is possible to obtain a two-phase system which consists of two liquid phases.

If appropriate, co-catalysts can be additionally used in the process according to the invention, and these can be employed in quantities of 1 to 100 mol %, relative to the phase transfer catalyst. Suitable co-catalysts are alkali metal halides, in particular alkali metal bromides and iodides, such as sodium bromide or potassium iodide.

The process according to the invention can be carried out especially at temperatures from 0° to 130° C., preferably 30° to 60° C.

It should be regarded as a further advantage of the process according to the invention that the p-allylphenols are obtained in a purity which enables them to be used directly for many puposes. If necessary, the pure p-allylphenols can also be prepared by conventional separation methods and purification methods.

The phenols and allyl halides are known starting materials. The phase transfer catalysts are commercially available.

The p-allylphenols of the formula I, which are obtainable, for example, by the process according to the invention, can be used as lubricant additives and as a starting material for antioxidants and further lubricant additives.

In lubricants, the compounds of the formula I develop excellent extreme-pressure and anti-wear properties, in addition to a good antioxidant and anticorrosive action.

The compounds of the formula I are, even in very small amounts, active as extreme-pressure additives in lubricants. Thus, mineral lubricating oils and synthetic lubricating oils and mixtures thereof, to which 0.001 to 5% by weight, relative to the lubricant, and preferably 0.02 to 3% of a compound of the formula I have been added, display excellent extreme-pressure lubrication properties which manifest themselves by greatly reduced wear phenomena on the friction surfaces which are to be lubricated. The lubricants concerned are known to those skilled in the art and are described, for example, in "Schmiermittel Taschenbush [Lubricants Handbook]" (Hüthig Verlag, Heidelberg. 1974).

The lubricating oil formulation can additionally also contain other additives, such as antioxidants, metal passivators, rust inhibitors, viscosity index improvers, pour point depressants, dispersants/detergents and other antiwear additives; these are added to improve certain properties of the base oil.

Examples of antioxidants are:

(a) alkylated and non-alkylated aromatic amines and mixtures thereof, for example dioctyldiphenylamine, mono-t-octylphenyl-α- and -β-naphthylamines, phenothiazine, dioctylphenothiazine, phenyl-α-naphthylamine and N,N-di-sec.-butyl-p-phenylenediamine.

(b) Sterically hindered phenols, for example 2,6-di-tert.-butyl-p-cresol, 4,4'-bis-(2,6-diisopropylphenol), 2,4,6-triisopropylphenol, 2,2'-thio-bis-(4-methyl-6-tert.-butylphenol) and 4,4'-methylene-bis-(2,6-di-tert.-butylphenol).

(c) Alkyl, aryl or alkaryl phosphites, for example trinonyl phosphite, triphenyl phosphite and diphenyl decyl phosphite.

(d) Esters of thiodipropionic acid or thiodiacetic acid, for example dilauryl thiodipropionate or dioctyl thiodiacetate.

(e) Salts of carbamic acids and dithiophosphoric acids, for example antimony diamyl-dithiocarbamate and zinc diamyl dithiophosphate.

(f) Combinations of two or more of the above antioxidants, for example an alkylated amine and a sterically hindered phenol.

Examples of metal passivators are:

(a) for copper, for example benzotriazole, tetrahydrobenzotriazole, 2-mercaptobenzothiazole, 2,5-dimercaptothiadiazole, salicylidene-propylenediamine and salts of salicylaminoguanidine.

(b) For lead, for example, sebacic acid derivatives, quinizarin and propyl gallate.

(C) Combination of two or more of the above additives.

Examples of rust inhibitors are:

(a) Organic acids and their esters, metal salts and anhydrides, for example N-oleoyl-sarcosine, sorbitane monooleate, lead naphthenate and dodecenylsuccinic anhydride.

(b) Nitrogen-containing compounds, for example:
   I. primary, secondary or tertiary aliphatic or cycloaliphatic amines and amine salts of organic and inorganic acids, for example: oil-soluble alkylammonium carboxylates.
   II. Heterocyclic compounds, for example substituted imidazolines and oxazolines.

(c) Phosphorus-containing compounds, for example amine salts of partial esters of phosphoric acid.

(d) Sulfur-containing compounds, for example barium dinonylnaphthalenesulfonates and calcium petroleum sulfonates.

(e) Combinations of two or more of the above additives.

Examples of viscosity index improvers are polymethacrylates, vinylpyrrolidone/methacrylate copolymers, polybutenes, olefine copolymers and styryl/acrylate copolymers.

Examples of pour point depressants are polymethacrylates and alkylated naphthalene derivatives.

Examples of dispersants/detergents are polybutenylsuccinimides, polybutenylphosphonic acid derivatives and superbasic magnesium, calcium and barium sulfonates and phenolates.

Examples of other antiwear additives are compounds containing sulfur and/or phosphorus and/or halogen, such as sulfurised vegetable oils, zinc dialkyl dithiophosphates, tritolyl phosphate, chlorinated paraffins, alkyl disulfides and aryl disulfides.

The examples which follow explain the invention.

Preparation of 4-allyl-2,6-di-tert.-butylphenol

EXAMPLE 1

80 g (2 mols) of powdered sodium hydroxide are added, at about 35° C. under a stream of nitrogen gas, to a mixture of 412 g (2 mols) of 2,6-di-tert.-butylphenol, 67.5 g (0.128 mol) of tricaprylmethylammonium chloride, 15 g (0.126 mol) of potassium bromide and 400 ml of toluene, and the mixture is heated to 50° C. in the course of 15 minutes. 199 g (2.6 mols) of allyl chloride are added dropwise to the suspension in the course of 30 minutes. The suspension is stirred for 4 hours at 48° to 53° C. 400 ml of water and 5 ml of 36 percent by volume aqueous hydrochloric acid are added with stirring, and the aqueous phase is then separated off. The organic phase is dried over anhydrous sodium sulfate and freed from toluene in vacuo at 10 to 150 mm Hg. The 4-allyl-2,6-di-tert.-butylphenol obtained in this way in a very high yield can be used without further purification as a lubricant additive.

EXAMPLE 2

In a process analogous to that of Example 1, the reaction of 206 g (1 mol) of 2,6-di-tert.-butylphenol and 115 g (1.5 mols) of allyl chloride in 200 ml of toluene, in the presence of 80 g (2 mols) of powdered sodium hydroxide and 31 g (0.061 mol) of hexadecyltributylphosphonium bromide gives a very high yield of 4-allyl-2,6-di-tert.-butylphenol after 2 hours at 48° to 53° C.

EXAMPLE 3

In a procedure analogous to that of Example 1, the reaction of 206 g (1 mol) of 2,6-di-tert.-butylphenol and 115 g (1.5 mols) of allyl chloride in 200 ml of toluene, in the presence of 52 g (1.3 mols) of powdered sodium hydroxide and 16 g (0.05 mol) of tetrabutylammonium bromide, gives 4-allyl-2,6-di-tert.-butylphenol in a very high yield after 3 hours at 48° to 53° C.

No co-catalyst is used in Examples 2 and 3.

APPLICATION EXAMPLES

EXAMPLE 4

The WSD value was determined, using a Shell four-ball machine (Tentative Method IP 239/69, extreme-pressure and wear lubricant test for oils and greases, four-ball machine).

WSD=wear scan diameter in mm. This is the mean wear diameter under a load of 40 kg applied for 1 hour.

The base oil used was Vitrea 41 (Shell tradename).

Concentration of the stabiliser: 1% by weight, relative to the base oil.

| Test results: | |
|---|---|
| Stabiliser | WSD (mm) |
| none | about 2.4 |
| 4-Allyl-2,6-di-tert.-butylphenol | 0.75 |

EXAMPLE 5

Oil-oxidation test, standard version according to ASTM D 2272 (Rotary Bomb Oxidation Test)

An oil sample of 50 ml of "Vitrea 41" brand mineral oil from Shell, to which 0.25 g of stabiliser had been added, is oxidised, in a glass vessel under an oxygen atmosphere, together with 5 ml of distilled water and a bright-polished, catalytically acting Cu spiral which has been washed with petroleum ether.

The glass vessel is located in a stainless steel bomb with a manometer. The bomb rotates axially at 100 revolutions per minute, under an angle of 30° to the horizontal, in an oil bath at 150° C. Initially, before heating up, the oxygen pressure is about 6 atmospheres (90 psi); at 150° C., it rises to almost 14 atmospheres (200 psi) and remains constant until the oxidation starts. The test is ended when the pressure has dropped by 1.7 atmospheres (25 psi). The time in minutes is recorded.

| Test results: | |
|---|---|
| Stabiliser | Minutes until the pressure has fallen by 25 psi |
| none | 16 |
| 4-Allyl-2,6-di-tert.butylphenol | 90 |

EXAMPLE 6

Oil-oxidation test according IP 280, "CIGRE"

Modified version with a soluble Cu and Fe catalyst. Conditions: Oxygen is introduced at 150° C. for 4 hours (4 liters of O$_2$/hour).

Determination of the acid number after the end of the test; value in the table; mg of KOH consumed per g of test oil.

Stabiliser concentration: 0.5% by weight, relative to the test oil.

Test oil: "Vitrea 41" brand mineral oil from Shell.

| Test results: | |
|---|---|
| Stabiliser | mg of KOH/g |
| none | 3.6 |
| 4-Allyl-2,6-di-tert.-butylphenol | 0.71 |

What is claimed is:

1. A process for the preparation of a p-allylphenol, which is substituted in the ortho-position, of formula I

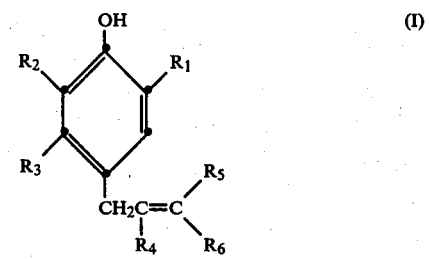

wherein
R$_1$ is C$_1$–C$_{12}$ alkyl, phenyl, C$_7$–C$_9$ aralkyl or C$_5$–C$_7$ cycloalkyl,
R$_2$ is hydrogen, chlorine, C$_1$–C$_{12}$ alkyl, phenyl, C$_7$–C$_9$ aralkyl or C$_5$–C$_7$ cycloalkyl,
R$_3$ is hydrogen or methyl, R$_4$, R$_5$ and R$_6$ independently of one another are hydrogen, phenyl, or C$_1$–C$_{20}$ alkyl, with the proviso that, as alkyl radicals, R$_4$, R$_5$ and R$_6$ in total contain 1 to 20 C atoms, and which is essentially free of allyl aryl ether, which comprises
reacting a phenol of formula II

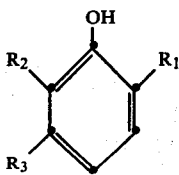

where $R_1$, $R_2$ and $R_3$ are defined as above, with an allyl halide of formula III

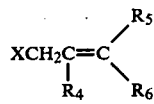

where $R_4$, $R_5$ and $R_6$ are defined as above, and X is halogen, in a molar equivalent ratio of phenol to allyl halide of 2:1 to 1:2, in the presence of a base selected from the group consisting of the alkali metal hydroxides, the alkali metal carbonates and the alkali metal alcoholates having 1 to 6 carbon atoms, with at least one mol equivalent of base for each mol equivalent of phenol, at a temperature of 0° to 130° C., and in the presence of 0.001 to 50 mol. %, based on the phenol of formula II, of a phase transfer catalyst selected from the group consisting of the quaternary salts, cyclic polyethers, open-chain polyethers, N-alkylphosphoramides, methylene-bridged phosphorus oxides and methylene-bridged sulfur oxides.

2. A process according to claim 1, wherein a p-allylphenol of the formula I is prepared from a phenol of the formula II and an allyl halide of the formula III, in which $R_1$ and $R_2$ independently of one another are $C_1$–$C_8$ alkyl, and $R_2$ additionally can be hydrogen, $R_3$ is hydrogen or methyl and $R_4$, $R_5$ and $R_6$ independently of one another are hydrogen or $C_1$–$C_6$ alkyl, with the proviso that, as alkyl radicals, $R_4$, $R_5$ and $R_6$ in total contain 1 to 6 C atoms.

3. A process according to claim 1, wherein a p-allylphenol of the formula I is prepared from a phenol of the formula II and an allyl halide of the formula III, in which $R_1$ and $R_2$ independently of one another are tert.-butyl, tert.-amyl or 1,1,3,3-tetramethylbutyl and $R_3$, $R_4$, $R_5$ and $R_6$ are hydrogen.

4. A process according to claim 1, wherein 4-allyl-2,6-di-tert.-butylphenol is prepared.

5. A process according to claim 1, wherein the base used is an alkali metal hydroxide.

6. A process according to claim 1, wherein the base used is sodium hydroxide.

7. A process according to claim 1, wherein the phase transfer catalyst used is a quaternary salt.

8. A process according to claim 1, wherein the phase transfer catalyst used is a quaternary ammonium or phosphonium salt.

9. A process according to claim 1, wherein additionally a solvent is used.

10. A process according to claim 9, wherein the solvent used is an aromatic hydrocarbon.

11. A lubricant composition containing a p-allylphenol of the formula I, obtainable according to claim 1, as a lubricant additive.

* * * * *